United States Patent
Raut et al.

(10) Patent No.: US 12,365,662 B2
(45) Date of Patent: Jul. 22, 2025

(54) PROCESS FOR 4-(HYDROXYMETHYL)-5-METHYL-1,3-DIOXOL-2-ONE

(71) Applicant: PIRAMAL PHARMA LIMITED, Mumbai (IN)

(72) Inventors: Changdev Raut, Mumbai (IN); Ajay Kumbhar, Mumbai (IN); Tanaji Jadhav, Mumbai (IN); Ganesh Wagh, Mumbai (IN); Ashutosh Jagtap, Mumbai (IN); Sivakumar Rallapalli, Mumbai (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 734 days.

(21) Appl. No.: 17/761,868

(22) PCT Filed: Oct. 8, 2020

(86) PCT No.: PCT/IB2020/059472
§ 371 (c)(1),
(2) Date: Mar. 18, 2022

(87) PCT Pub. No.: WO2021/070113
PCT Pub. Date: Apr. 15, 2021

(65) Prior Publication Data
US 2022/0372011 A1    Nov. 24, 2022

(30) Foreign Application Priority Data
Oct. 9, 2019    (IN) .............................. 201921040813

(51) Int. Cl.
C07D 317/36    (2006.01)
B01J 27/08    (2006.01)
C07D 317/40    (2006.01)

(52) U.S. Cl.
CPC ............ *C07D 317/36* (2013.01); *B01J 27/08* (2013.01)

(58) Field of Classification Search
CPC ....... C07D 317/36; C07D 317/40; B01J 27/08
See application file for complete search history.

(56) References Cited

U.S. PATENT DOCUMENTS 5,416,208 A    5/1995    Perrone et al.
9,233,955 B2 *    1/2016    Bansal .................... A61P 9/12

FOREIGN PATENT DOCUMENTS

JP    5925386 A    2/1984
JP    59212488 A    12/1984

OTHER PUBLICATIONS

ISR for International Application PCT/IB2020/059472 mailed Jan. 15, 2021.
Written Opinion for International Application PCT/IB2020/059472 mailed Jan. 15, 2021.

* cited by examiner

*Primary Examiner* — Sun Jae Yoo
(74) *Attorney, Agent, or Firm* — Ladas & Parry LLP

(57) ABSTRACT

The present invention relates to an improved process for 4-(Hydroxymethyl)-5-methyl-1,3-dioxol-2-one (I). The process involves reaction of compound of formula (II) with sodium acetate in presence of catalytic amount of potassium iodide in dimethyl formamide solvent at 25-30° C. to give 5-methyl-2-oxo-1,3-dioxol-4-yl)methyl acetate (IV) which was further Acid hydrolysed by IPA·HCl in Isopropyl alcohol solvent to yield 4-(hydroxymethyl)-5-methyl-1,3-dioxol-2-one (I).

10 Claims, No Drawings

PROCESS FOR 4-(HYDROXYMETHYL)-5-METHYL-1,3-DIOXOL-2-ONE

RELATED APPLICATION

This application is an application under 35 U.S.C. 371 of International Application No. PCT/IB2020/059472 filed 8 Oct. 2020, which claims priority from Indian Application 201921040813 filed 9 Oct. 2019, the disclosures of which are incorporated in their entirety by reference herein.

FIELD OF THE INVENTION

The present invention relates to a method for the preparation of 4-(Hydroxymethyl)-5-methyl-1,3-dioxol-2-one (I).

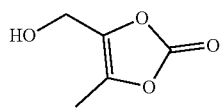

(I)

Particularly, the present invention relates to an improved, commercially viable, production friendly and cost effective process for the preparation of 4-(Hydroxymethyl)-5-methyl-1,3-dioxol-2-one (I).

4-(Hydroxymethyl)-5-methyl-1,3-dioxol-2-one (I) can be further used as intermediate for the manufacturing of Azilsartan kamedoxomil by any method known in the art.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

4-(Hydroxymethyl)-5-methyl-1,3-dioxol-2-one (I) is a central precursor of (5-methyl-2-oxo-1,3-dioxol-4-yl) methyl-2-ethoxy-1-{[2'-(5-oxo-4,5-dihydro-1,2,4-oxodiazol-3-yl)biphenyl-4-yl]methyl}-1H-benzimidazole-7-carboxylate (herein after referred as "Azilsartan kamedoxomil"). 4-(Hydroxymethyl)-5-methyl-1,3-dioxol-2-one (I) has a CAS number of 91526-18-0, and a molecular formula of $C_5H_6O_4$.

JPS59212488A describes a method of preparing 4-(Hydroxymethyl)-5-methyl-1,3-dioxol-2-one (I), wherein reaction of compound of formula (II) with potassium formate results in (5-methyl-2-oxo-1,3-dioxol-4-yl)methyl formate which is not isolated and on refluxing in methanol give compound (I).

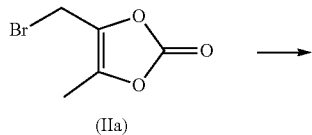

(IIa)

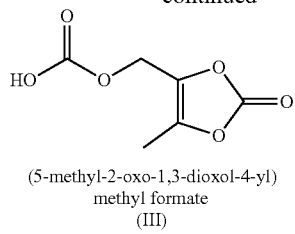

(5-methyl-2-oxo-1,3-dioxol-4-yl) methyl formate
(III)

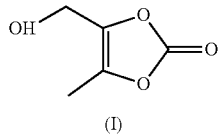

(I)

U.S. Pat. No. 9,233,955B2 discloses the preparation of 4-(Hydroxymethyl)-5-methyl-1,3-dioxol-2-one (I), which involves use of formic acid in Acetonitrile and reaction is performed at 60-65° C. in 79% yield.

In addition to the above cited patents (US'955 and J'488), JPS5925386A and U.S. Pat. No. 5,416,208A also disclose the preparation of compound (I). The J'386 uses sulfonates as starting material in acetonitrile while US'208 uses silver nitrate as reagent in acetonitrile.

However, the processes disclosed in the above mentioned prior art has the following observed limitations:
  Use of Formic acid as reagent is not cheaper and feasible at industrial scale;
  Use of acetonitrile as a reaction solvent makes the process expensive;
  The prior art reactions are carried out at 60-65° C., which make the process undesirable at large scale operations;
  The overall yield of the final product is not promising, which makes technological mode of production unfavorable.

Inventors of the present invention have developed an improved process that addresses the problems associated with the processes reported in the prior art.

Accordingly, the present invention provides a straightforward and scalable process of preparation of compound (I). The reported method is simple, efficient, cost effective, environmentally friendly and commercially scalable for large-scale operations.

SUMMARY OF THE INVENTION

In one aspect, the present invention relates to an improved process for preparation of 4-(Hydroxymethyl)-5-methyl-1,3-dioxol-2-one (I).

In another aspect, the present invention relates to an improved process for the preparation of 4-(Hydroxymethyl)-5-methyl-1,3-dioxol-2-one (I),

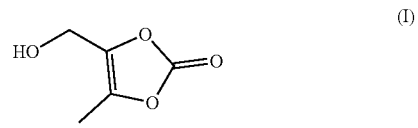

(I)

comprising;
  (a) reacting compound of formula (II) with alkali metal acetate in a solvent and optionally in presence of a catalyst to obtain (5-methyl-2-oxo-1,3-dioxol-4-yl) methyl acetate (IV), and optionally isolating compound of formula (IV);

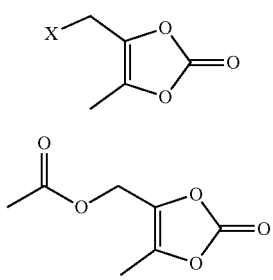

(b) treating the compound of formula (IV) with a solvent to produce 4-(Hydroxymethyl)-5-methyl-1,3-dioxol-2-one (I).

DETAILED DESCRIPTION OF THE INVENTION

Accordingly, the present invention relates to an improved process for the preparation of 4-(Hydroxymethyl)-5-methyl-1,3-dioxol-2-one (I), comprising;
(a) reacting compound of formula (II) with alkali metal acetate in a solvent and optionally in presence of a catalyst to obtain (5-methyl-2-oxo-1,3-dioxol-4-yl) methyl acetate (IV), and optionally isolating compound of formula (IV);

(b) treating the compound of formula (IV) with an acid solution in a solvent to produce 4-(Hydroxymethyl)-5-methyl-1,3-dioxol-2-one (I).

The present invention also relates to the process, wherein step (b) can be carried out without isolating the intermediate compound (IV) of step (a).

The alkali metal acetate used in step (a) is selected from sodium acetate, potassium acetate, etc.

The solvent(s) used in step (a) and (b) is selected from an ether solvent such as tetrahydrofuran, cyclopentyl methyl ether, 2-methyltetrahydrofuran, diethyl ether, dioxane, 1,4-dioxane, 1,2-dioxane or 1,3-dioxane; an alcoholic solvent such as methanol, ethanol, isopropanol, t-amyl alcohol, t-butyl alcohol or hexanol; halogenated solvent such as dichloromethane, 4-bromotoluene, diiodomethane, carbon tetrachloride, chlorobenzene or chloroform; ketone such as acetone; an aprotic solvent such as acetonitrile, N,N-dimethyl formamide (DMF), N,N-dimethyl acetamide, dimethyl sulfoxide (DMSO) or N-methylpyrrolidone (NMP); an aromatic solvent such as toluene, xylene or benzene; water or a mixture thereof.

The catalyst used in step (a) is selected from metal halide like sodium iodide, potassium iodide, potassium bromide or sodium bromide.

The acid solution used in step (b) is prepared by dissolving suitable acid in an alcoholic solvent, wherein the acid is selected from inorganic acids such as hydrochloric acid, hydrobromic acid, nitric acid, sulfuric acid; and the alcoholic solvent is selected from methanol, ethanol, isopropanol, t-amyl alcohol, t-butyl alcohol or hexanol.

The step (a) is carried out at a temperature in the range of 25° C. to 35° C.

The product formed in step (a) can be used in the next stage with or without isolation of the product.

The whole synthetic scheme of preparation of 4-(Hydroxymethyl)-5-methyl-1,3-dioxol-2-one (I) according to the present invention can be represented as below:

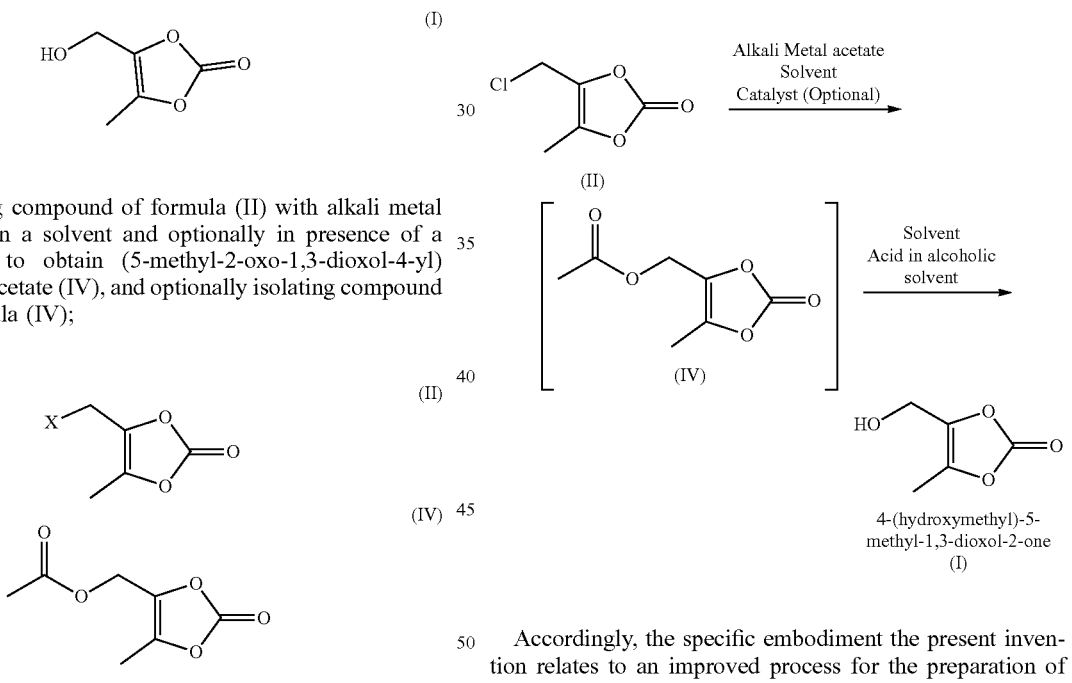

Accordingly, the specific embodiment the present invention relates to an improved process for the preparation of 4-(Hydroxymethyl)-5-methyl-1,3-dioxol-2-one (I),

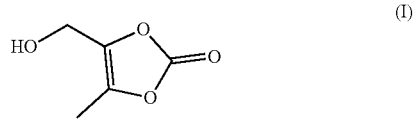

comprising;
(a) reacting compound of formula (II) with sodium acetate in a solvent and optionally in presence of a catalyst to obtain (5-methyl-2-oxo-1,3-dioxol-4-yl)methyl acetate (IV), and optionally isolating compound of formula (IV);

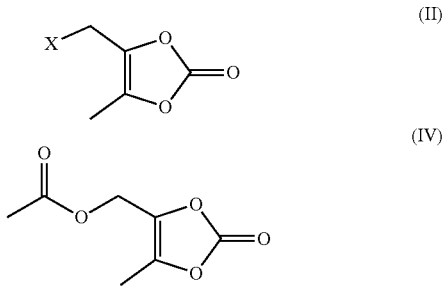

(b) treating the compound of formula (IV) with an acid solution in a solvent to produce 4-(Hydroxymethyl)-5-methyl-1,3-dioxol-2-one (I).

The present invention also relates to the process, wherein step (b) can be carried out without isolating the intermediate compound (IV) of step (a).

The solvent(s) used in step (a) and (b) is selected from an ether solvent such as tetrahydrofuran, cyclopentyl methyl ether, 2-methyltetrahydrofuran, diethyl ether, dioxane, 1,4-dioxane, 1,2-dioxane or 1,3-dioxane; an alcoholic solvent such as methanol, ethanol, isopropanol, t-amyl alcohol, t-butyl alcohol or hexanol; halogenated solvent such as dichloromethane, 4-bromotoluene, diiodomethane, carbon tetrachloride, chlorobenzene or chloroform; ketone such as acetone; an aprotic solvent such as acetonitrile, N,N-dimethyl formamide (DMF), N,N-dimethyl acetamide, dimethyl sulfoxide (DMSO) or N-methylpyrrolidone (NMP); an aromatic solvent such as toluene, xylene or benzene; water or a mixture thereof.

The catalyst used in step (a) is selected from metal halide like sodium iodide, potassium iodide, potassium bromide or sodium bromide.

The acid solution used in step (b) is prepared by dissolving suitable acid in an alcoholic solvent, wherein the acid is selected from inorganic acids such as hydrochloric acid, hydrobromic acid, nitric acid, sulfuric acid; and the alcoholic solvent is selected from methanol, ethanol, isopropanol, t-amyl alcohol, t-butyl alcohol or hexanol.

The step (a) is carried out at a temperature in the range of 25° C. to 35° C.

The product formed in step (a) can be used in the next stage with or without isolation of the product.

The whole synthetic scheme of preparation of 4-(Hydroxymethyl)-5-methyl-1,3-dioxol-2-one (I) according to the present invention can be represented as below:

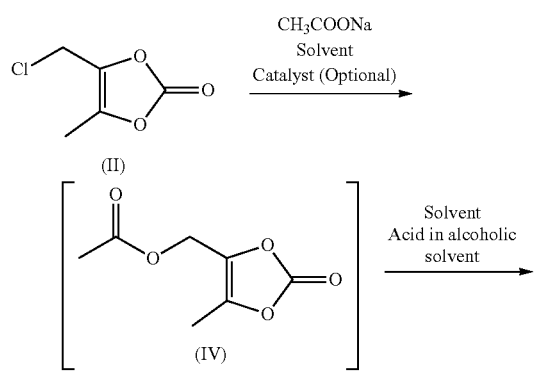

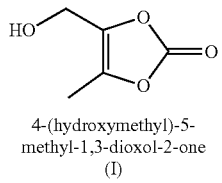

4-(hydroxymethyl)-5-
methyl-1,3-dioxol-2-one
(I)

According to the invention, the overall yield of 4-(Hydroxymethyl)-5-methyl-1,3-dioxol-2-one (I) as obtained by using the process of the present invention is at least about 89-91% yield with purity of at least about 85% by HPLC.

Thus, the present invention uses sodium acetate and dimethyl formamide, which is easily available at cheaper rate as compared to that of formic acid and acetonitrile. Further, the reaction of the present invention is carried out at room temperature. Thereby, reducing reaction time or production time and manufacturing cost of 4-(Hydroxymethyl)-5-methyl-1,3-dioxol-2-one (I). The present invention results into yield of at least about 89-91% with purity of at least 85% by HPLC, thereby, making the process efficient, economic and industrially viable.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example 1

Preparation of 4-(Hydroxymethyl)-5-methyl-1,3-dioxol-2-one (I)

Reactor was rinsed with DMF (20 ml) at 25-35° C. DMF (80 ml) and sodium acetate (66.5 g) and sodium iodide (2.5 g) and 4-(chloromethyl)-5-methyl-1,3-dioxol-2-one (MDX-Cl) (100 g) were charged into the reactor. The reaction mass was stirred for 18-20 h at 25-35° C. After completion of reaction, dimeralized (DM) water (300 ml) and toluene (100 ml) was charged into reaction mass. Aqueous layer was extracted with toluene (100 ml) twice. Combined organic layer was washed with DM water (100 ml). Charcoal (10 g) was charged into organic layer at 25-35° C., stirred for 20-30 min, filtered through hyflow bed, and washed with Toluene (50 ml) at 25-35° C. Organic layer was distilled out under vacuum at 40-50° C. After distillation reaction mass was cooled at 20-25° C. and 5% IPA·HCl (500 ml) was charged at 20-25° C. Reaction mass was heated at 30-35° C. and stirred for 24-28 h at 30-35° C. Reaction mass was distilled out under vacuum at 30-40° C. and obtained oil was degassed under vacuum at 30-40° C. Unloading of the product was carried out under N₂ atmosphere. [Yield w/w: 80 g; Yield (%): 91%; HPLC Purity: 85]

Example 2

Preparation of 4-(Hydroxymethyl)-5-methyl-1,3-dioxol-2-one (I)

Reactor was rinsed with DMF (20 ml) at 25-35° C. DMF (80 ml) and Toluene (100 ml) and Sodium Acetate (66.5 g) and Sodium Iodide (2.5 g) and 4-(chloromethyl)-5-methyl- 1,3-dioxol-2-one (MDX-Cl) (100 g) were charged into reactor. The reaction mass was stirred for 18-20 h at 25-35° C. After completion of reaction, DM water (300 ml) was charged into the reaction mass. Aqueous layer was back extracted with Toluene (100 ml) twice. Combined organic layer was washed with DM water (100 ml). Charcoal (10 g) was charged into organic layer at 25-35° C., stirred for 20-30 min and filtered through hyflow bed and washed with Toluene (50 ml) at 25-35° C. Organic layer was distilled out under vacuum at 40-50° C. After distillation reaction mass was cool at 20-25° C. and 5% IPA·HCl (500 ml) was charged at 20-25° C. Reaction mass was heated at 30-35° C. and stirred for 24-28 h at 30-35° C. Reaction mass was distilled out under vacuum at 30-40° C. and obtained oil was degassed under vacuum at 30-40° C. Unloading of the product was carried out under $N_2$ atmosphere. [Yield w/w: 78 g; Yield (%): 89%; HPLC Purity: 85]

We claim:

1. An improved process for the preparing 4-(Hydroxymethyl)-5-methyl-1,3-dioxol-2-one (I),

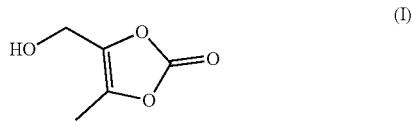

comprising;
(a) reacting compound of formula (II) with alkali metal acetate in a solvent and optionally in presence of a catalyst to obtain (5-methyl-2-oxo-1,3-dioxol-4-yl) methyl acetate (IV), and optionally isolating compound of formula (IV);

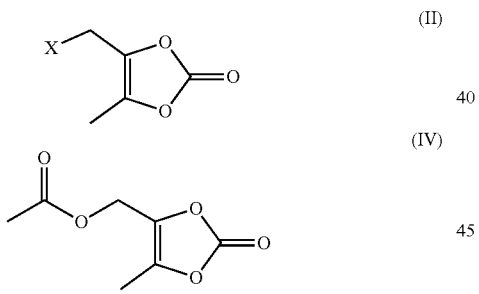

(b) treating the compound of formula (IV) with an acid solution in a solvent to produce 4-(Hydroxymethyl)-5-methyl-1,3-dioxol-2-one (I).

2. The process as claimed in claim 1, wherein the alkali metal acetate used in step (a) is selected from sodium acetate or potassium acetate.

3. The process as claimed in claim 1, wherein the solvent used in step (a) is an aprotic solvent.

4. The process as claimed in claim 3, wherein the aprotic solvent use in step (a) is selected from acetonitrile, N,N-dimethyl formamide (DMF), N,N-dimethyl acetamide, dimethyl sulfoxide (DMSO), N-methylpyrrolidone (NMP), or a mixture thereof.

5. The process as claimed in claim 1, wherein the catalyst used in step (a) is a metal halide.

6. The process as claimed in claim 5, wherein the metal halide is selected from sodium iodide, potassium iodide, potassium bromide or sodium bromide.

7. The process as claimed in claim 1, wherein the acid used in step (b) is an inorganic acid selected from hydrochloric acid, hydrobromic acid, nitric acid or sulfuric acid.

8. The process as claimed in claim 1, wherein the solvent used in step (b) for preparing acid solution is an alcoholic solvent selected from methanol, ethanol, isopropanol, t-amyl alcohol, t-butyl alcohol or hexanol.

9. The process as claimed in claim 1, wherein the step (a) is carried out at a temperature range of 25° C. to 35° C.

10. An improved process for the preparation of 4-(Hydroxymethyl)-5-methyl-1,3-dioxol-2-one (I),

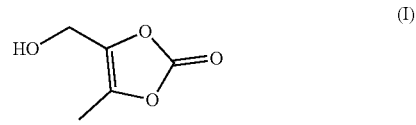

comprising;
(a) reacting compound of formula (II) with alkali metal acetate in a solvent and optionally in presence of a catalyst to obtain (5-methyl-2-oxo-1,3-dioxol-4-yl) methyl acetate (IV);

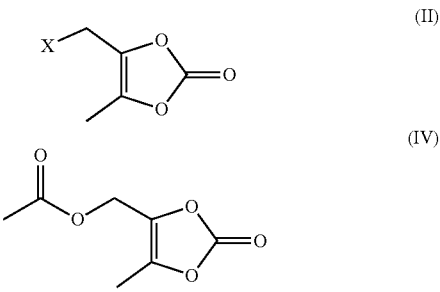

wherein, the said reaction is carried out at a temperature in the range of 25° C. to 35° C.;
(b) treating the compound of formula (IV) with an acid solution in a solvent to produce 4-(Hydroxymethyl)-5-methyl-1,3-dioxol-2-one (I).

* * * * *